United States Patent [19]

Wang

[11] 4,147,976

[45] Apr. 3, 1979

[54] DEVICE FOR TESTING AND CALIBRATING MOISTURE MEASURING INSTRUMENT

[76] Inventor: Robert O. Wang, 2744 S. 61st St., Milwaukee, Wis. 53219

[21] Appl. No.: 841,760

[22] Filed: Oct. 13, 1977

[51] Int. Cl.² .................................................. G01R 27/26
[52] U.S. Cl. ..................................... 324/61 R; 73/1 R; 324/74; 340/515
[58] Field of Search .................... 324/61 R, 74, 65 P; 73/1 R, 1 F; 340/410, 214, 225

[56] References Cited

U.S. PATENT DOCUMENTS

| | | | |
|---|---|---|---|
| 2,540,658 | 2/1951 | DeGiers et al. | 324/61 R X |
| 2,654,862 | 10/1953 | Petersen | 324/65 P |
| 2,693,575 | 11/1954 | Greenwood et al. | 324/61 R |
| 2,806,376 | 9/1957 | Wood | 73/1 F |
| 2,869,359 | 1/1959 | Offermann | 324/65 P |
| 3,348,408 | 10/1967 | Engborg | 73/1 F |
| 4,066,951 | 1/1978 | Wang | 324/61 R |

Primary Examiner—Stanley T. Krawczewicz
Attorney, Agent, or Firm—James E. Nilles

[57] ABSTRACT

A testing and calibration device is provided for a known type of electrical instrument for measuring moisture in a grain sample. The instrument comprises a sample-receiving test cell in the form of a cylindrical container having a concentric electrode therewithin and operates on the principle that the intensity of an electrostatic field in the test cell changes in proportion to the amount of moisture in the grain sample. The testing and calibration device, which serves as synthetic sample or substitute for a controlled grain sample of known size, dielectric constant and moisture content, comprises concentrically arranged inner and outer cylindrical dielectric members defining a sealed cylindrical space therebetween which contains a metal component of appropriate size and shape and sufficient liquid added during manufacture to duplicate the electrical characteristics of the controlled grain sample. The liquid may take the form of water or a mixture of water and an antifreeze agent. A thermometer is embodied in the device to provide ambient temperature information sometimes required for test purposes.

9 Claims, 6 Drawing Figures

DEVICE FOR TESTING AND CALIBRATING MOISTURE MEASURING INSTRUMENT

BACKGROUND OF THE INVENTION

1. Field of Use

This invention relates generally to a device for testing and calibrating a known type of electrical instrument which is used for measuring the moisture content of a sample of grain or other particulate material.

2. Description of the Prior Art

U.S. Pat. No. 2,693,575, issued Nov. 2, 1954 to Greenwood et al for "Moisture Determining Device for Materials" discloses an electrical instrument which is used for measuring the amount of moisture in a sample of grain or other particulate material. This instrument, which operates on electrostatic principles, generally comprises a test cell for holding a material sample of known type and size whose moisture content is to be determined and further comprises a comparative capacitance unit. The test cell comprises a cylindrical metal container open at its upper end and closed at its bottom end by an insulating disc and a cylindrical metal central electrode (insulated on the outside of a plastic sleeve) concentrically mounted within the container on the insulating disc in spaced relationship with the container. The test cell is, in effect, a capacitor and the container and the central electrode serve as the electrodes which are part of a resonant electrical circuit of the comparative capacitance unit. In operation, the resonant circuit is first balanced with the test cell empty. The material sample is then added to the cell, thus increasing its capacitance and the circuit is then rebalanced by means of a calibrated standard condenser and the change in capacity as indicated by this condenser, and a suitable indicator, is then correlated to the moisture content. In practice, moisture determining instruments of this character are accurately calibrated during manufacture but are subject to miscalibration during use as the sensitive electrical components therein age or deteriorate during use. Accordingly, a means in the form of a manually adjustable trimmer condenser is provided to enable the instrument to be accurately recalibrated periodically. Heretofore, testing of the instrument for accuracy and recalibration required the use of a controlled grain sample which took the form of a measured amount of grain or other material having known dielectric characteristics and moisture content. Such samples are available in sealed containers from the U.S. government through specified channels of distribution which exist in the trade, and recalibration using such samples is carried out on a periodic basis. While this method of testing and recalibrating moisture meters is very accurate and reliable, the procedures for obtaining the controlled samples are cumbersome and no testing or calibration was heretofore possible unless the controlled sample was available. U.S. patent application Ser. No. 729,128, filed Oct. 4, 1976, which was allowed on Aug. 29, 1977 as U.S. Pat. No. 4,066,951 on Jan. 3, 1978 and assigned to the same assignee as the present application, discloses a calibration apparatus which comprises a dielectric member for slideable insertion between the container wall and the electrode to a predetermined distance to effect a change in field intensity, means for holding the dielectric member in a desired position in the test cell, a pointer detachably connectable to the test cell, and a graduated scale on the dielectric member for cooperation with the pointer to indicate visually a numeric value which corresponds to a numeric value which will appear as the visual meter readout if the instrument is calibrated correctly.

SUMMARY OF THE PRESENT INVENTION

In accordance with the present invention, there is provided an improved device for testing and calibrating a known type of electrical instrument which is used for measuring the amount of moisture in a sample of grain or other particulate material. The instrument operates on the principle that the intensity of an electrostatic field will change in proportion to the moisture content of a material sample of predetermined type and size placed in the field, i.e., in proportion to the actual dielectric constant of the sample. The instrument comprises a test cell for receiving the sample and the cell comprises a container having a concentrically disposed electrode therewithin which are part of a resonant electrical circuit; means for establishing a balanced electrostatic field of known intensity in the space between the container wall and electrode; means for measuring the change in field intensity (i.e., an increase in capacitance) effected by the moisture content of the sample and for providing a visual meter readout in the form of a numeric value correlated to the change in field intensity (and thus moisture content); and means for readjusting or recalibrating the instrument to re-establish the desired field intensity in the event of an undesired change therein. The test and calibration device in accordance with the present invention serves as a synthetic sample of material and is a substitute for a controlled sample of the actual material to be tested for moisture content. The device comprises two concentrically arranged hollow cylindrical dielectric members defining a sealed space or chamber therebetween, which space has a metal component of predetermined size therein and is filled with an amount of liquid necessary to cause the total device to exhibit the electrical characteristic necessary to effect the predetermined change in field intensity. The calibration device is constructed so as to exhibit the electrical characteristics of a government-furnished controlled sample of grain, for example. The metal component, which could take any shape but which is preferably a sheet of metal foil of cylindrical shape, brings the total electrical value or characteristic of the device close to the desired range. Manufacturing tolerances and variations in size and construction in component parts of the device which would otherwise cause inaccuracies in the electrical effect of the device are then easily and accurately finally compensated for during manufacture by adding an amount of liquid to the chamber before sealing the same as is necessary to achieve the desired electrical value. Furthermore, whereas the apparatus disclosed in aforementioned U.S. patent application Ser. No. 729,128 enabled calibration of the instrument while the latter was set in the "calibrate" mode, the device in accordance with the invention enables calibration of the apparatus while the latter is in the "operate" mode, thereby making it easier for the average user of the machine to test and to ascertain miscalibration, since any calibration error which registers in the "operate" mode provides the final meter readout with which the user is normally concerned.

Calibration apparatus in accordance with the present invention offers several advantages over the prior art. For example, it enables regular and frequent recalibration of all types of existing moisture meters which employ the electrostatic field principle. It eliminates the need to obtain controlled samples of grain or other particulate materials heretofore necessary for recalibration purposes thereby reducing the expense and trouble of obtaining the controlled sample and also enables the moisture meter to be recalibrated on a more frequent basis. Also, since any test of calibration error is exhibited to the user in the "operate" mode rather than in the "calibrate" mode of the instrument being readied for use, the calibration test is more meaningful to the average user. Calibration apparatus in accordance with the present invention is relatively economical to manufacture and is simple and reliable in use. Once a controlled grain sample is obtained and a prototype calibration device is constructed to exhibit the characteristics thereof, the prototype can then be used as the measurement for the subsequent production of commercial devices. Also, the use of a desired amount of liquid to enable final tuning and adjustment enables a high degree of accuracy to be achieved in a very simple way during manufacture. Other objects and advantages of the invention will hereinafter appear.

DESCRIPTION OF A PREFERRED EMBODIMENT

Figure 1:
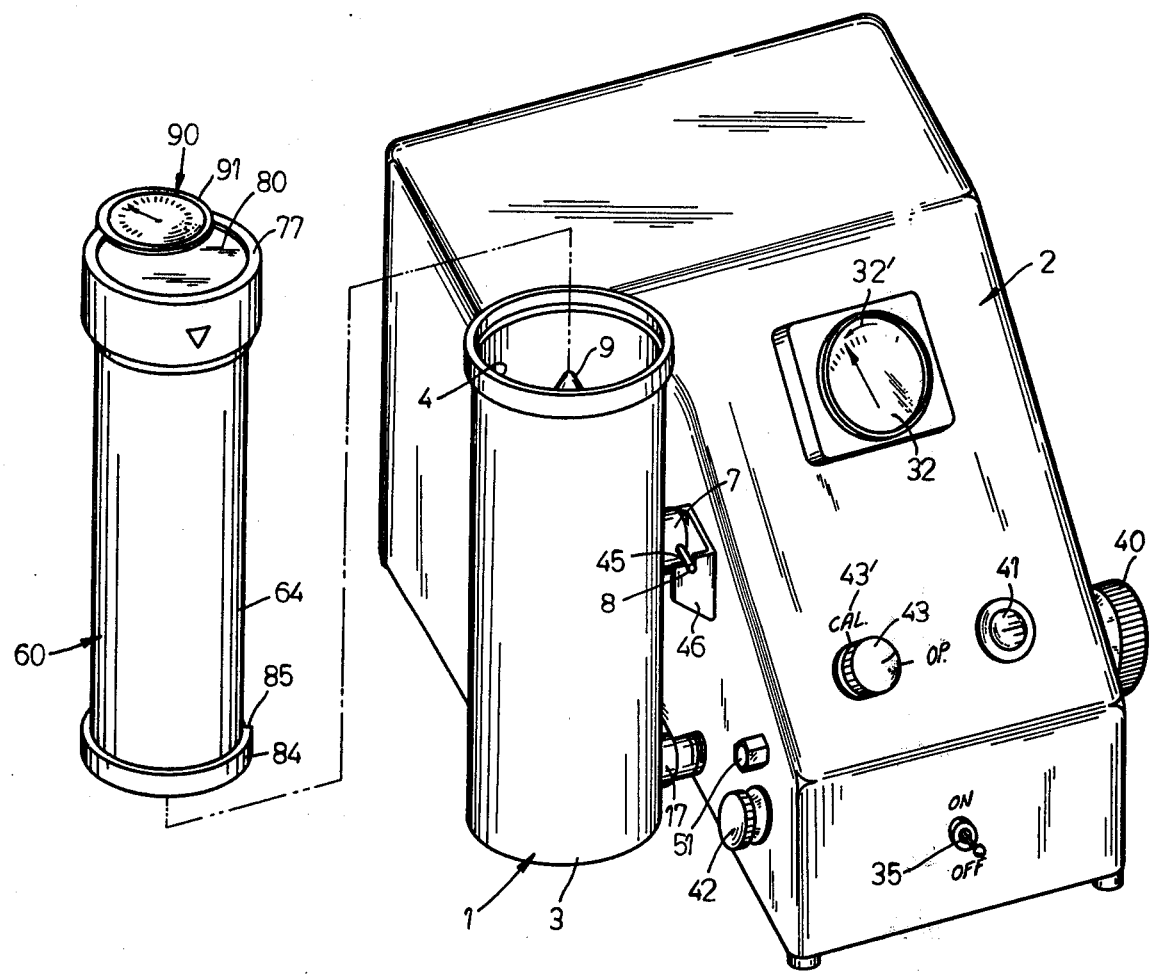
FIG. 1 is a perspective view of a moisture measuring instrument, its associated test cell, and a test and calibration device therefor in accordance with the invention.
Figure 2:
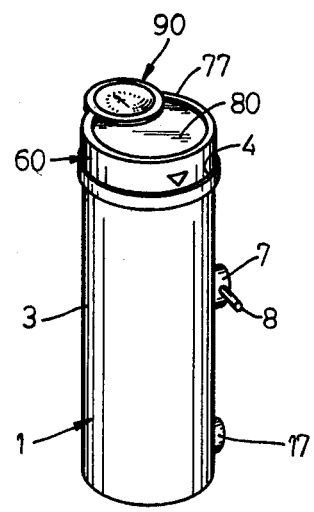
FIG. 2 is a perspective view of the test cell shown in FIG. 1 and showing it in association with the test and calibration device in accordance with the invention.
Figure 4:
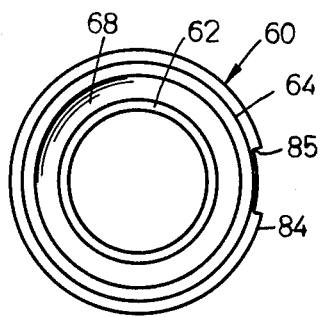
FIG. 4 is a bottom plan view, in reduced scale, of the test and calibration device shown in FIG. 3.

Referring to FIG. 1 of the drawing, there is shown a moisture measuring instrument comprising a test cell 1 and a cooperative capacitance unit 2 for use therewith. FIGS. 1, 2, 3, 4, and 5 show a device 60 in accordance with the invention for testing and calibrating the moisture measuring instrument, which device is hereinafter described in detail.

Figure 3:
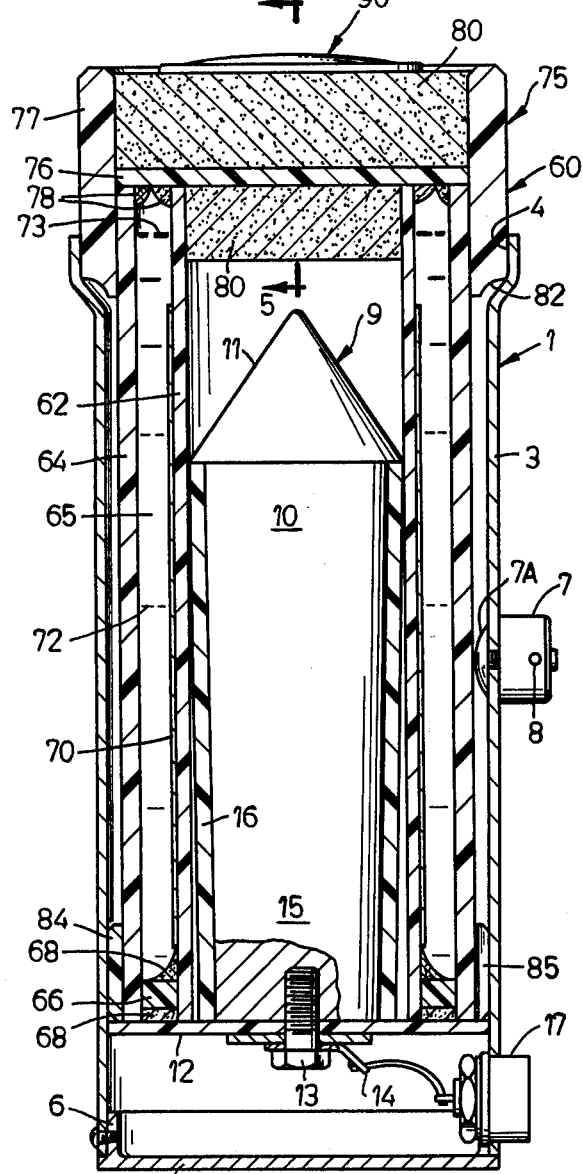
FIG. 3 is an enlarged cross-sectional view of the test cell and test and calibration device shown in FIG. 2.

Reference to FIG. 3 of the accompanying drawings will show the details of construction of the test cell 1 and it will be seen that it consists of a cylindrical container 3 being open at the upper end 4 thereof and closed by means of a base plate 5 which is detachably secured to the base of the cylinder by screws or the like passing through the wall of the cylinder and an upstanding annular shoulder 6 formed upon the base plate 5.

The aforementioned outer container 3 constitutes one of the electrodes of this test cell and is connected to the unit 2 by means of a hanger 7 extending from the side of the cylinder 3, said hanger including a pair of outstanding prongs 8 which engage the unit in a manner hereinafter to be described.

The central electrode 9 of the test cell comprises an inverted truncated conical portion 10 surmounted by a material dispersal cap 11 which ensures that material poured into the cell is distributed evenly around the central electrode.

This electrode is secured concentrically within the cylindrical container 3 upon an insulating disc 12 spanning the container in spaced relationship above the end cap 5. A bolt 13 passes through a connector 14, through the disc 12, and is screw-threadably engagable within the base 15 of the central electrode 9 thus maintaining the central electrode in equal spaced relationship to the walls of the cylinder 3. A plastic sleeve 16 surrounds the central electrode and prevents the possibility of a direct connection between electrodes should the material being tested act as a high resistance conductor. Furthermore, due to the concentration of field at the central electrode in such a concentric arrangement, the sleeve serves to prevent small portions of the sample, which might differ from the main body of the sample, from having a disproportionate effort on the whole.

Means are provided to eliminate the increased effective dielectric constant of the material when loaded into the cell which is caused if the material packs and becomes more dense at the lower ends thereof. In this embodiment, this has been minimized by forming the main portion 10 of the central electrode in the inverted truncated cone as hereinbefore described, thereby giving an increased distance between the central electrode and the walls of the outer container at the base thereof, this distance gradually decreasing towards the upper ends of the two electrodes.

The aforementioned connector 14 extends from the base of the central electrode to a coaxial terminal 17 also provided on the wall of the outer container 3 immediately below the aforementioned hanger 7 and this, together with the hanger 7 enables the test cell 1 to be connected and disconnected from the unit 2 as desired. The coaxial terminal connects the cell electrically to the unit 2.

Figure 6:
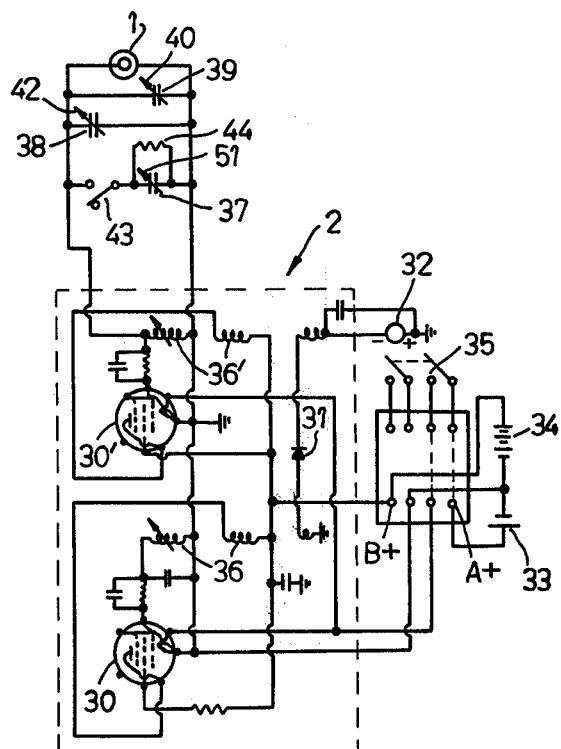
FIG. 6 is a schematic diagram of the electrical circuit of the moisture measuring instrument shown in FIG. 1.

The electronic unit 2 associated with the test cell 1 takes the form of a comparative capacitance unit the schematic wiring diagram of which is shown in detail in FIG. 6. The circuit comprises a pair of oscillators 30 and 30' linked by a coupling circuit which include a germanium diode 31 and a milliammeter 32. Power is supplied to the circuit by means of the two batteries 33 and 34, the former supplying the A+ current to the filaments and the latter, the B+ current as indicated, a multiple switch 35 being provided to switch the circuit on and off as required.

The resonant circuit of the oscillator 30 includes an inductance 36 and the frequency of this oscillator is fixed. The resonant circuit of the other oscillator 30' includes an inductance 36' and four capacitances, condensers 37, 38, and 39, and the cell 1 which is shown schematically in the wiring diagram of FIG. 6. Condenser 39 is calibrated variable standard condenser operated by knob 40 in FIG. 1, the calibration showing by means of the dial 41 on the face of the instrument. Condenser 38 is the trimming condenser and is operated by knob 42 on the opposite side of the instrument to knob 40. Condenser 37 is a fixed standard condenser having an associated selector switch 43 (CAL or OP) and a resistor 44 in circuit therewith of such a value as to make the condenser 37 the equivalent in both dielectric constant and loss factor to a standard sample of grain having a given moisture content placed in the cell. In this example, the sample has been arbitrarily set at 150 grams having 15% moisture, the grain being wheat.

A recalibration capacitor 37 which is manually adjustable by means of a knob 51 shown, when required, uses the calibration apparatus in accordance with the invention as hereinafter described.

Proceeding now to describe the operation, the empty cell 1 is first connected to the side of the unit 2 by means of the hanger 7 and coaxial terminal 17, it being understood that the latter connects the cell electronically to the resonant circuit of the oscillator 30' as signified in FIG. 6. The aforementioned prongs 8 of the hanger 7 engage within slots 45 provided in offstanding lugs 46 situated at the left-hand side of the instrument as shown in FIG. 1.

The main switch 35 is then moved to the "on" position thus connecting the batteries 33 and 34 to the circuit. In this connection, although batteries have been shown as a source of power in this embodiment, it will be appreciated that, if desired, a power pack may be supplied so that the unit 2 may be connected to the main source of electrical supply normally present in most places where the device is to be used.

The switch 43 is then closed thus bringing into the circuit the calibrating condenser 37 and its resistor 44 and, in this connection, in FIG. 1, this closed position is indicated by the letters "CAL" designated by number 43'. The calibrated variable condenser 39 is then turned until a predetermined dial reading shows under the hair-line on dial 41, this position being a calibrating position and being marked on the dial of this condenser. Trimming condenser 38 is now adjusted by means of knob 42 until there is a minimum flow of current in the coupling circuit between oscillators 30 and 30', this minimum flow being shown on the meter 32. For convenience, an arrow 32' is provided on the dial of the meter with the head directed towards the left thereof with relation to FIG. 1, this arrow indicating the direction that the needle of the meter should move in order to indicate the minimum current flow.

When this minimum flow is obtained, the instrument is calibrated ready for use and the switch 43 is opened, being turned from CAL to OP, thus taking the standard condenser 37 out of the circuit. In this connection, the letters "OP" are shown on the face of the instrument and represents "operate" as contrasted to "calibrate."

In use, and assuming that the instrument 2 is in proper calibration, a sample of the grain or material to be tested in then carefully weighed as specified on charts supplied with the instrument, which has been calibrated in the range from 40° F. to 104° F. It is important that the temperature of the sample be ascertained prior to the tests being taken and this can be done by any standard method. This weighed sample is now placed within the test cell 1. It will be seen that the sample of the material now loaded within the test cell effects the circuit capacity of the oscillator 30' thus detuning same causing a current to flow in the coupling circuit. Therefore, power will be transferred from one oscillator to another in an effort to keep the two locked in frequency and, in this connection, it should be noted that a change in the circuit capacity of oscillator 30' of as little as 0.01 mmf will cause a change in the circulating current as indicated by the meter. In order to bring the tuning of the oscillator 30' into alignment with that of oscillator 30, the variable calibrated condenser 39 is rotated by means of knob 40 until once again there is a minimum current flow within the coupling circuit as indicated by the meter 32. In other words, the needle of this meter 32 should be as far to the left of the dial as possible (with reference to FIG. 1). The reading of the calibrated condenser shown on meter 41 is then compared to a chart prepared for the material being tested whereupon the percentage moisture can be read from the chart. In this connection, it will be appreciated that charts are provided for any material being tested, these charts being prepared by the correlation of many determinations of moisture by laboratory methods.

Means are provided to check the over-all accuracy of the instrument at any time, but usually before the aforementioned sample of grain is inserted, thus enabling the operator to ensure that the readings taken are accurate determinations of the moisture present in the material being tested. This procedure entails calibrating the instrument as hereinabove described while cell 1 is empty (i.e., by tuning main switch 35 to "on," placing control knob 43 in "CAL," adjusting knob 40 to provide a predetermined reading such as "53" under hairline 41, adjusting knob 42 to swing the needle of meter 32 to its lowest leftward position and then switching knob 43 from "CAL" to "OP") and then employing the test and calibration device 60 in accordance with the invention to determine if the instrument is in proper adjustment and, if not, to then enable desired recalibration (usually at the factory) by means of the knob 51 to readjust recalibration capacitor 37. More specifically, with the apparatus 2 in the operate position, device 60 is inserted all the way into test cell 1 and knob 40 is adjusted to set the dial 41 at some predetermined value, such as the value "43," to which the device 60 has been designed. If the apparatus 2 is in proper calibration the needle of meter 32 will move to its lowest leftward point (which lowest point will be slightly different than the lowest point reached during the aforedescribed calibration steps). If the apparatus 2 is in calibration, the dial 41 will continue to register the value "53," for example, and if it does not, this is an indication that the apparatus is out of adjustment.

It is to be understood that most instruments such as 2 are intended to be tested and calibrated at standard calibration values, such as "33," "53," and "63." It is to be further understood that the device 60 hereinafter described in detail is designed, for example, to provide a value "53" and this in turn is based on a value "53" of a controlled sample having a value "53" used during construction of a prototype device 60. As a practical matter, however, the device 60 is of such accuracy and of such size and electrical characteristic as to be able to provide proper test results at any value in the range of from "25" to "75". This range could be extended above or below the values 25 through 75.

As FIGS. 1, 3, 4, and 5 best show, the test and calibration device 60 is provided for slideable insertion between the wall of container 3 and the electrode 9 all the way to the bottom of the test cell 1 to effect a predetermined change in field intensity and to thereby provide a numeric value, such as value "53," which will appear as the visual meter readout on scale 41, if the instrument 2 is calibrated correctly.

More specifically, device 60 takes the general form of a hollow cylinder closed at its upper end and open at its lower end which is adapted to be slid over central electrode 9 in test cell 1 into the space between the electrode 9 and container 3.

The device 60 comprises hollow cylindrical inner and outer members 62 and 64, respectively, fabricated of rigid electrically non-conductive dielectric material, such as Plexiglas or Conolite or the like, and concentrically arranged so as to define a cylindrical space or chamber 65 therebetween. The lower end of chamber 65 is sealed by means of a ring 66, fabricated of electrically non-conductive dielectric material such as Plexiglas or Conolite, which is disposed in the space between the lower ends of the members 62 and 64 and sealed in place by a dielectric adhesive 68 such as air-hardening liquid rubber cement. An electrically conductive component 70 of appropriate size, shape, and material for contributing to necessary electrical characteristic of device 60 is disposed within chamber 65 and, for example, takes the form of a cylinder of sheet metal, such as thin aluminum foil, which surrounds inner cylindrical member 62. Component 70 may take other forms, such as individual strips of metal, or a spirally wound single strip, and may or may not be attached in place, as by an adhesive. Chamber 65 is filled with a liquid 72 to such level 73 as is necessary to cause device 60 to exhibit the same electrical characteristics as the controlled grain sample it is intended to simulate. The liquid 72 may take the form of water, but preferably comprises a mixture of water and alcohol or other type of antifreeze agent to prevent the sealed-in liquid from being frozen and causing damage to the device 60, since such devices are often transported or left outdoors in freezing temperatures. A 50%—50% mixture of water and antifreeze agent was used in an actual embodiment of the invention. The upper end of chamber 65 is sealed by means of a cover assembly 75 which includes a flat sheet or disc 76 and a collar 77, both of dielectric material. Disc 76, which overlies the upper end of chamber 65 and the central opening of inner member 62, is sealed in place by means of a dielectric rubber cement type of adhesive 78 which is applied to the upper end edges of the cylinders 62 and 64. Collar 77 slips over the end of the outer cylinder 64 and is secured in place by dielectric potting compound or adhesive 80 which is also applied to the undersurface of disc 76. Collar 77 includes a lower machined flange 82 which ensures that there is proper engagement with container 3 of test cell 1. Device 60 also includes a lower collar 84 which provides for a snug fit of the device within container 3. Collar 84 is notched at 85 to accommodate screw 7A.

Figure 5:
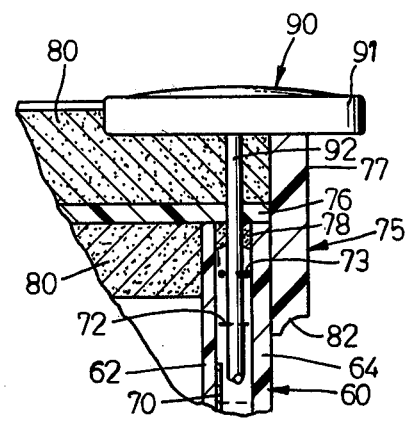
FIG. 5 is a cross-sectional view of the thermometer of the test and calibration device taken on line 5—5 of FIG. 3.

As FIG. 5 shows, device 60 includes a commercially available thermometer 90 having a body portion 91 and a probe 92 which extends downwardly in sealed relation into chamber 65. Thermometer 90, which is physically secured in place by the potting compound 80, is a convenience available to the user of device 60 who may need to know temperature in the course of a sample test. Once a prototype device 60 is fabricated, any desired number of duplicate devices can be fabricated for use and sale.

The test and calibration device 60 is employed as follows. First, the instrument is to be calibrated as hereinbefore described, as if to put it in readiness to test a particular sample of material. More specifically, switch 35 is turned on, switch 43 is turned to CAL, knob 42 is used to bring needle 32 to its lowest point, and switch 43 is turned to OP. Use is now made of the hereinbefore mentioned charts for this purpose. However, instead of using a controlled sample of material, the test and calibration device in accordance with the invention is employed instead.

The device 60 is inserted within test cell 1. As will be understood, the device 60 used will be one which is precalibrated or designed to simulate a controlled sample of a particular type of material. The calibrated variable condenser 39 is then adjusted by knob 40 until a predetermined dial reading, such as "53," shows under the hair-line at 41, this position being a calibrating position and being so marked on the dial of this instrument. Trimming condenser 38 was previously adjusted by means of knob 42 until there was a minimum flow of current in the coupling circuit between oscillators 30 and 30', this minimum flow being shown on the meter 32. When a minimum flow is still obtained on meter 32, the instrument is calibrated ready for use provided, of course, that the numberal "53" still remains as the scale reading under the hair-line of meter 41. If such correspondence occurs, the instrument is properly calibrated. If, however, the dial reading "53" does not result in the needle of meter 32 does not remain at its low point, this indicates that the instrument is out of calibration, and such misregistration is corrected at the factory by moving knob 51 to effect the necessary adjustment of recalibration capacitor 37 in the conventional manner.

In practice, the user of the instrument does not normally attempt to recalibrate the instrument as this is preferably done at the factory because in many instances, other internal adjustments to the instrument need to be made. However, the user of the instrument employs apparatus in accordance with the invention to check the accuracy of his instrument usually at the commencement of each days work of for each cargo of grain to be tested.

It is to be understood that although capacitor 37 is shown herein as the capacitor whereby the instrument is recalibrated, other types of instruments having other components requiring adjustment for purposes of recalibration are intended to be within the scope of the present invention.

I claim:

1. A device for simulating a controlled sample of material of known size, dielectric constant and moisture control, and to be placed in a test cell of an electrical instrument which is used to measure the moisture content of a sample of material, said test cell comprising a hollow cylindrical container having an electrode concentrically arranged therewithin, said device comprising:
   a cylindrical body for placement in said container, said body having an axially extending cylindrical opening therein for receiving said electrode and comprising:
   concentrically arranged inner and outer hollow cylindrical members of dielectric material defining a cylindrical chamber therebetween;
   dielectric means for sealing said chamber at both ends and supporting said members relative to each other;
   an electrically conductive component sealed within said chamber, said electrically conductive component being in the form of a cylindrical sheet and surrounding said inner dielectric member;
   and a quantity of liquid within said chamber, said quantity being sufficient to cause the device to exhibit the same electrical characteristics as said controlled sample.

2. A combination according to claim 1 wherein said liquid comprises water.

3. A combination according to claim 2 wherein said liquid comprises a mixture of water and an antifreeze agent.

4. A combination according to claim 1 including a thermometer mounted on said device.

5. A device according to claim 1 wherein said dielectric means for sealing the lower end of said chamber comprises a ring fabricated of electrically non-conductive dielectric material which is disposed in the space between the lower ends of said cylindrical members and sealed in place by a dielectric adhesive.

6. A device according to claim 5 wherein said dielectric means for sealing the upper end of said chamber comprises a cover assembly which includes a flat sheet and a collar, both of dielectric material, wherein said flat sheet overlies the upper end of said chamber and the central opening of inner member and is sealed in place by means of a dielectric adhesive, and wherein said collar slips over the end of said outer cylinder and is secured in place by dielectric potting compound or adhesive which is also applied to the undersurface of said disc.

7. A device according to claim 6 wherein said collar includes a lower flange which ensures that there is proper engagement with the container of said test cell.

8. A device according to claim 7 wherein said device also includes a lower collar which provides for a snug fit of said device within said container.

9. A device according to claim 4 wherein said thermometer has a body portion and a probe which extends downwardly in sealed relation into said chamber and is physically secured in place by potting compound.

* * * * *